(12) United States Patent
Zhong et al.

(10) Patent No.: US 9,187,507 B2
(45) Date of Patent: Nov. 17, 2015

(54) ACYCLIC NUCLEOSIDE PHOSPHONATE DERIVATIVES AND MEDICAL USES THEREOF

(75) Inventors: Bohua Zhong, Beijing (CN); Xinhua He, Beijing (CN); Yongguang Wang, Beijing (CN); He Liu, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 13/514,749

(22) PCT Filed: Jun. 21, 2010

(86) PCT No.: PCT/CN2010/000902
§ 371 (c)(1),
(2), (4) Date: Jul. 19, 2012

(87) PCT Pub. No.: WO2011/069322
PCT Pub. Date: Jun. 16, 2011

(65) Prior Publication Data
US 2012/0322764 A1   Dec. 20, 2012

(30) Foreign Application Priority Data

Dec. 10, 2009 (CN) .......................... 2009 1 0252161

(51) Int. Cl.
*C07F 9/6561* (2006.01)
*A61K 31/683* (2006.01)

(52) U.S. Cl.
CPC .................................. *C07F 9/65616* (2013.01)

(58) Field of Classification Search
CPC .................................................. C07F 9/65616
USPC ..................................... 544/276, 244; 514/81
See application file for complete search history.

(56) References Cited

U.S. PATENT DOCUMENTS

| 5,840,716 A | 11/1998 | Ubasawa et al. |
| 2003/0153534 A1 | 8/2003 | Ubasawa et al. |
| 2004/0063668 A1 | 4/2004 | Choi et al. |

FOREIGN PATENT DOCUMENTS

| CN | 1164534 A | 11/1997 |
| CN | 1670024 A | 9/2005 |
| CN | 1827627 A | 9/2006 |
| CN | 1986553 | 6/2007 |
| CN | 10166981 A | 11/2007 |
| CN | 101085785 | 12/2007 |
| EP | 0 785 208 A1 | 7/1997 |
| JP | 07-070159 A | 3/1995 |
| JP | 09-255695 A | 9/1997 |
| JP | 2000-515866 A | 11/2000 |
| JP | 2004-518675 A | 6/2004 |
| JP | 2005-508924 A | 4/2005 |
| WO | WO 98/04569 A1 | 2/1998 |
| WO | WO 01/64693 A1 | 9/2001 |
| WO | WO 02/057288 A1 | 7/2002 |
| WO | WO 03/028737 A1 | 4/2003 |
| WO | WO 2009/105513 A2 | 8/2009 |

OTHER PUBLICATIONS

Random House Kernerman Webster's College Dictionary, 2010 K Dictionaries Ltd. Copyright 2005, 1997, 1991 by Random House.*
Panel on Treatment of HIV-Infected Pregnant Women and Prevention of Perinatal Transmission. Recommendations for Use of Antiretroviral Drugs in Pregnant HIV-1-Infected Women for Maternal Health and Interventions to Reduce Perinatal HIV Transmission in the United States.http://aidsinfo.nih.gov/contentfiles/lvguidelines/PerinatalGL.pdf. AccessOct. 2013.*

(Continued)

*Primary Examiner* — Samantha Shterengarts
*Assistant Examiner* — Matt Mauro
(74) *Attorney, Agent, or Firm* — Sterne, Kessler, Goldstein & Fox P.L.L.C.

(57) ABSTRACT

The present invention relates to an acyclic nucleoside phosphonate derivative and medical uses thereof. Specifically, the present invention relates to an acyclic nucleoside phosphonate derivative of Formula I having strong potency against viruses, such as hepatitis B virus, and low cytotoxicity, or a pharmaceutically acceptable salt, isomer, hydrate or solvate thereof, wherein $R_1$ is H or methyl; each $R_2$ is independently —$R_3$ or —$OR_3$, each $R_3$ is independently $C_1$-$C_8$ alkyl, $C_3$-$C_8$ cycloalkyl. The present invention further relates to a process for preparing the compounds of Formula I, a pharmaceutical composition comprising the compound, and the medical uses of the compound. The acyclic nucleoside phosphonate derivative of the present invention has activity against virus such as hepatitis B virus and good in vivo behavioral traits.

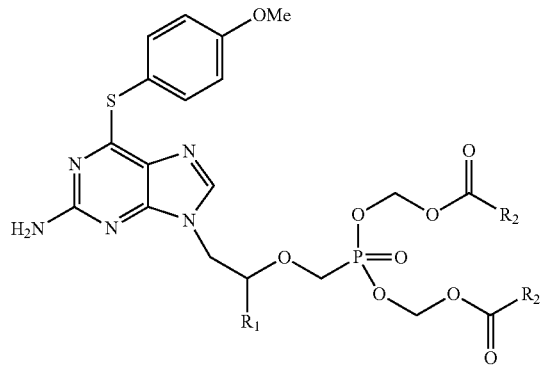

16 Claims, No Drawings

(56) References Cited

OTHER PUBLICATIONS

Lau, G.K.K., Hepatitis B reactivation after chemotherapy: two decades of clinical research 2008 Hepatol. Int. 2: 152-162.*
Barditch-Crovo, P., Anti-Human ImmunodeficiencyVirus (HIV) Activity, Safety, and Pharmacokinetics of Adefovir Dipivoxil (9-[2-(bis-pivaloyloxymethyl)- phosphonylmethoxyethyl]denine) in HIV-infected Patients, J. Infect. Dis., 1997, 176(2), 406-413.*
Yuan, L.-C., Degradation Kinetics of Oxycarbonyloxymethyl Prodrugs of Phosphonates in Solution, Pharm. Res., 2001, 18(2), 234-237.*
Wu, D., Anti-hepatitis B virus activity and toxicity of a novel nucleoside analogues in vitro, J. Jilin Univ. 33 (2007) 422-426.*
International Search Report for PCT/CN2010/00902; I.A. fd: Jun. 21, 2010, mailed Oct. 21, 2010 from The State Intellectual Property Office, the P.R. China, Beijing, China.
International Preliminary Report on Patentability, Chapter I of the Patent Cooperation Treaty, including the Written Opinion for PCT/CN2010/000902; I.A. fd: Jun. 21, 2010, issued Jun. 12, 2012, from the International Bureau of WIPO, Geneva, Switzerland.
Chan, C et al., "Clinical Pharmacokinetics of Alamifovir and Its Metabolites," Antimicrob. Agents Chemother. 49: 1813-1822 (May 2005), Am. Soc. Microbiology, Washington, D.C.
Kamiya, N. et al., "Antiviral Activities of MCC-478, a Novel and Specific Inhibitor of Hepatitis B Virus," Antimicrob. Agents Chemother.46: 2872-2877 (Sep. 2002), Am. Soc. Microbiology, Washington, D.C.
Kioko, S et al., "Novel Nucleoside Analogue MCC-478 (LY582563) Is Effective against Wild-Type or Lamivudine-Resistant Hepatitis B Virus," Antimicrob. Agents Chemother. 46: 2602-2605 (Aug. 2002), Am. Soc. Microbiology, Washington, D.C.
Extended European search report inlcuding the supplementary European search report and the European search opinion, for EP Application No. 10835359.0, dated Apr. 25, 2013, European Patent Office, Rijswijk, Netherlands.
Chemical Abstracts Service, Columbus, OH, Accession No. 2006:940072, Y. Jin et al., "Preparation of purine derivatives as antiviral agents for treatment for Hepatits B," abstract, retrieved from STN, XP002695611.
"Notification of Office Action" for JP patent application No. 2012-542339, mailed Feb. 20, 2014, Japanese Patent Office, Tokyo, Japan.
Farquhar, D et al., "Biologically reversible phosphate-protective groups," J Pharm Sci, Mar. 1983; 72(3): 324-325, American Pharmaceutical Assn, Easton, PA.
Krise, JP et al., "Prodrugs of phosphates, phosponatcs, and phosphinates," Advanced Drug Delivery Reviews, 1996, vol. 19, pp. 287-310, Elsevier Science Publishers, Amsterdam, Netherlands.

* cited by examiner

ACYCLIC NUCLEOSIDE PHOSPHONATE DERIVATIVES AND MEDICAL USES THEREOF

TECHNICAL FIELD

The present invention relates to an acyclic nucleoside phosphonate derivative having a potent activity against viruses, such as hepatitis B virus, and a low cytotoxicity, a process for preparing the same and uses thereof in the manufacture of a medicament for the treatment of viral infections such as an infection caused by hepatitis B virus.

BACKGROUND ART

Viral hepatitis such as hepatitis B is an important and major disease threatening the life and health of people, and the fundamental approach for treatment of hepatitis B is an antiviral treatment. At present, clinically effective drugs against hepatitis B virus are mainly interferons and lamivudine. However, the effective rate of interferon treatment is merely 30-50%, and has dose-dependent toxicity and side-effects. Lamivudine has pronounced activity against hepatitis B virus, but may result in drug resistance during long-term administration. After consecutive administration for 2 years, the incidence rate of drug resistance is up to 40-50%, thereby inducing serious consequences such as acute episode of hepatitis.

Nucleotide analogues are not phosphorylated in cells, and thus can overcome the drug resistance of lamivudine, and do not generate drug resistance per se. Adefovir dipivoxil as one of the representative drugs had been approved for marketing in Europe and the United States. However, Adefovir dipivoxil has certain cytotoxicity, and may produce nephrotoxicity during clinical use. In addition, similar to lamivudine, after drug withdrawal of Adefovir dipivoxil, replication rebound of hepatitis B virus may occur and induce the recurrence of hepatitis B.

According to the successful experiences in the research of anti-HIV drugs, COCKTAIL treatment of using drugs in combination can effectively overcome drug resistance and accelerate the clearance of virus. The number of people with infection of hepatitis B is 10 times or more the number of people with HIV infection, but the clinically effective drugs against hepatitis B virus are few.

European patent EP0785208 discloses a series of acyclic nucleoside phosphonate compounds of the following formula:

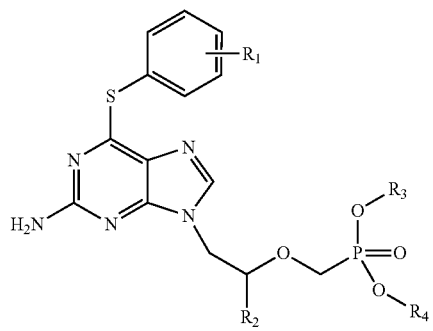

wherein, $R_1$ represents a substituent for occurrence once such as an alkoxy, and alkyl; $R_2$ represents hydrogen or an alkyl, $R_3$ and $R_4$ represent hydrogen, and an alkyl, etc.

Among them, the compound 2-amino-6-(4-methoxyphenylthio)-9-[2-[bis(2,2,2-trifluoroethyloxy) phosphono methoxy]propyl]-purine (MCC-478, Alamifovir) has been clinically investigated.

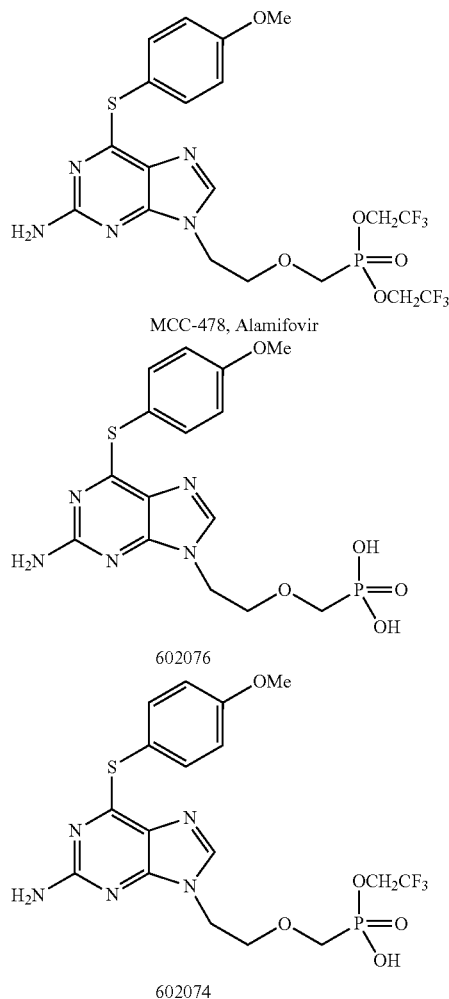

MCC-478 is a nucleotide with a new structure and is a new drug against hepatitis B virus. In the chemical structure, it is different from those known nucleosides as anti-hepatitis B drugs. MCC-478 molecule has a modified glycosyl and is further substituted with phenylthio at position-6 of nucleoside base mother nucleus. In pharmaceutical properties, MCC-478 also exhibits features different from other anti-HBV drugs, i.e., it inhibits the replication of viruses by inhibiting the initiating reaction and assembling reaction of protein synthesis (Clark Chan, et al. Clinical Pharmacokinetics of Alamifovir and Its Metabolites. Antivicrob Agents Chemother, 2005, 49(5):1813-1822); it has high selectivity and inhibition effect to HBV, and its in vitro activity is 20-80 times that of lamivudine, and 10-20 times that of adefovir. However, it has no activity against other retro viruses such as HIV and HSV (Kamiya N, et al. Antiviral activities of MCC-478, a novel and specific inhibitor of hepatitis B Virus. Antimicrob Agents Chemother 2002; 46(9):2872), thereby exhibiting unique pharmacological properties; MCC-478 also has inhibition effects on HBV strains with resistance to lamivudine (Suzane Kioko Ono-Nita, Oro-Nita S K, et al. Novel Nucleoside analogue MCC-478 (LY582563) is effective against wild-type or lamivudine-resistant hepatitis B virus. Antimicrob Agents Chemother 2002; 46: 2602-2605).

As a prodrug of the nucleotide analogue, MCC-478 releases the free acid (602076) and produces the effect against virus after entering the body and being hydrolyzed, but the results of pharmacokinetics showed that the major metabolite of MCC-478 in human body is nucleotide monoester (602074), the concentration of the free acid 602076 in blood is merely 1/10 of that of the monoester 602074 (Clark Chan, et al. Clinical Pharmaco-kinetics of Alamifovir and Its Metabolites. Antivicrob Agents Chemother, 2005, 49(5):1813-1822), while the cytotoxicity of the monoester 602074 ($CC_{50}$=548 µM) is significantly higher than that of MCC-478 and 602076 (both having $CC_{50}$>1000 µM) (Kamiya N, et al. Antiviral activities of MCC-478, a novel and specific inhibitor of hepatitis B Virus. Antimicrob Agents Chemother 2002; 46(9): 2872).

Currently, there is still a need to find a novel drug for clinical use which is effective against viruses such as hepatitis B virus, and especially has a high bioavailability.

DESCRIPTION OF THE INVENTION

The object of the present invention is to provide a novel and potent compound having an antiviral activity and especially high bioavailability. The present inventors have found a structurally novel group of compounds, which compounds have not only a good antiviral activity, but also unexpected good performances in vivo. The present invention has been accomplished based on the above finding.

SUMMARY OF THE INVENTION

The first aspect of the present invention provides an acyclic nucleoside phosphonate derivative or a pharmaceutically acceptable salt, isomer, hydrate or solvate thereof.

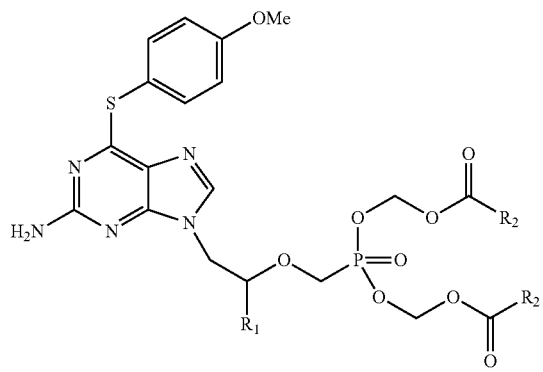

I wherein,
$R_1$ is selected from H or methyl;
each $R_2$ is independently selected from —$R_3$ or —$OR_3$; and
each $R_3$ is independently selected from $C_1$-$C_8$ alkyl, or $C_3$-$C_8$ cycloalkyl.

In the acyclic nucleoside phosphonate derivative or a pharmaceutically acceptable salt, isomer, hydrate or solvate thereof according to any embodiment of the first aspect of the present invention, $R_1$ is H.

In the acyclic nucleoside phosphonate derivative or a pharmaceutically acceptable salt, isomer, hydrate or solvate thereof according to any embodiment of the first aspect of the present invention, $R_1$ is methyl.

In the acyclic nucleoside phosphonate derivative or a pharmaceutically acceptable salt, isomer, hydrate or solvate thereof according to any embodiment of the first aspect of the present invention, two $R_2$ are the same.

In the acyclic nucleoside phosphonate derivative or a pharmaceutically acceptable salt, isomer, hydrate or solvate thereof according to any embodiment of the first aspect of the present invention, two $R_2$ are different.

In the acyclic nucleoside phosphonate derivative or a pharmaceutically acceptable salt, isomer, hydrate or solvate thereof according to any embodiment of the first aspect of the present invention, $R_2$ is —$R_3$.

In the acyclic nucleoside phosphonate derivative or a pharmaceutically acceptable salt, isomer, hydrate or solvate thereof according to any embodiment of the first aspect of the present invention, $R_2$ is —$OR_3$.

In the acyclic nucleoside phosphonate derivative or a pharmaceutically acceptable salt, isomer, hydrate or solvate thereof according to any embodiment of the first aspect of the present invention, one $R_2$ is —$R_3$, and the other $R_2$ is —$OR_3$.

In the acyclic nucleoside phosphonate derivative or a pharmaceutically acceptable salt, isomer, hydrate or solvate thereof according to any embodiment of the first aspect of the present invention, each $R_3$ for each occurrence is independently selected from $C_1$-$C_6$ alkyl or $C_3$-$C_6$ cycloalkyl.

In the acyclic nucleoside phosphonate derivative or a pharmaceutically acceptable salt, isomer, hydrate or solvate thereof according to any embodiment of the first aspect of the present invention, each $R_3$ for each occurrence is independently selected from $C_2$-$C_6$ alkyl or $C_4$-$C_6$ cycloalkyl.

In the acyclic nucleoside phosphonate derivative or a pharmaceutically acceptable salt, isomer, hydrate or solvate thereof according to any embodiment of the first aspect of the present invention, the alkyl (e.g., $C_1$-$C_8$ alkyl) is a straight or branched alkyl having the designated number of carbon (e.g., an alkyl having 1-8 carbon atoms).

In the acyclic nucleoside phosphonate derivative or a pharmaceutically acceptable salt, isomer, hydrate or solvate thereof according to any embodiment of the first aspect of the present invention, the cycloalkyl (e.g., $C_3$-$C_8$ cycloalkyl) is a cycloalkyl or cycloalkylalkyl having the designated number of carbon (e.g., a cycloalkyl containing 3-8 carbon atoms; or, e.g., a cycloalkylalkyl containing 3-8 carbon atoms, for example, cyclopropylmethyl or cyclohexylmethyl).

In the acyclic nucleoside phosphonate derivative or a pharmaceutically acceptable salt, isomer, hydrate or solvate thereof according to any embodiment of the first aspect of the present invention, each $R_3$ for each occurrence is independently selected from methyl, ethyl, propyl, isopropyl, butyl, isobutyl, tert-butyl, t-butyl, n-pentyl, isopentyl, neopentyl, cyclopropyl, cyclobutyl, cyclopentyl, cyclohexyl, or —CH($CH_2CH_3$)$_2$, etc.

In the acyclic nucleoside phosphonate derivative or a pharmaceutically acceptable salt, isomer, hydrate or solvate thereof according to any embodiment of the first aspect of the present invention, each $R_3$ for each occurrence is independently selected from ethyl, propyl, isopropyl, butyl, isobutyl, isopentyl, neopentyl, cyclopentyl, cyclohexyl, or —CH($CH_2CH_3$)$_2$, etc.

According to any embodiment of the first aspect of the present invention, the present invention provides an acyclic nucleoside phosphonate derivative selected from the group consisting of:

2-amino-6-(4-methoxyphenylthio)-9-{2-[bis(acetoxymethoxy)phosphonomethoxy]-ethyl}-purine;
2-amino-6-(4-methoxyphenylthio)-9-{2-[bis(propionyloxymethoxy)phosphonomethoxy]-ethyl}-purine;
2-amino-6-(4-methoxyphenylthio)-9-{2-[bis(butanoyloxymethoxy)phosphonomethoxy]-ethyl}-purine;
2-amino-6-(4-methoxyphenylthio)-9-{2-[bis(isobutanoyloxymethoxy)phosphonomethoxy]-ethyl}-purine;
2-amino-6-(4-methoxyphenylthio)-9-{2-[bis(pivaloyloxymethoxy)phosphonomethoxy]-ethyl}-purine;
2-amino-6-(4-methoxyphenylthio)-9-{2-[bis(cyclopentylformyloxymethoxy)phosphonomethoxy]-ethyl}-purine;
2-amino-6-(4-methoxyphenylthio)-9-{2-[bis(cyclohexylformyloxymethoxy)phosphonomethoxy]-ethyl}-purine;
2-amino-6-(4-methoxyphenylthio)-9-{2-[bis(ethyloxycarbonyloxymethoxy)phosphonomethoxy]-ethyl}-purine;
2-amino-6-(4-methoxyphenylthio)-9-{2-[bis(propyloxycarbonyloxymethoxy)phosphonomethoxy]-ethyl}-purine;
2-amino-6-(4-methoxyphenylthio)-9-{2-[bis(isopropyloxycarbonyloxymethoxy)phosphonomethoxy]-ethyl}-purine;
2-amino-6-(4-methoxyphenylthio)-9-{2-[bis(cyclopentyloxycarbonyloxymethoxy)phosphonomethoxy]-ethyl}-purine;
2-amino-6-(4-methoxyphenylthio)-9-{2-[bis(cyclohexyloxycarbonyloxymethoxy)phosphonomethoxy]-ethyl}-purine;
2-amino-6-(4-methoxyphenylthio)-9-{2-[bis(acetoxymethoxy)phosphonomethoxy]-propyl}-purine;
2-amino-6-(4-methoxyphenylthio)-9-{2-[bis(propionyloxymethoxy)phosphonomethoxy]-propyl}-purine;
2-amino-6-(4-methoxyphenylthio)-9-{2-[bis(butanoyloxymethoxy)phosphonomethoxy]-propyl}-purine;
2-amino-6-(4-methoxyphenylthio)-9-{2-[bis(isobutanoyloxy)phosphonomethoxy]-propyl}-purine;
2-amino-6-(4-methoxyphenylthio)-9-{2-[bis(pivaloyloxymethoxy)phosphonomethoxy]-propyl}-purine;
2-amino-6-(4-methoxyphenylthio)-9-{2-[bis(cyclopentylformyloxymethoxy)phosphonomethoxy]-propyl}-purine;
2-amino-6-(4-methoxyphenylthio)-9-{2-[bis(cyclohexylformyloxymethoxy)phosphonomethoxy]-propyl}-purine;
2-amino-6-(4-methoxyphenylthio)-9-{2-[bis(propyloxycarbonyloxymethoxy)phosphonomethoxy]-propyl}-purine;
2-amino-6-(4-methoxyphenylthio)-9-{2-[bis(propyloxycarbonyloxymethoxy)phosphonomethoxy]-propyl}-purine;
2-amino-6-(4-methoxyphenylthio)-9-{2-[bis(isopropyloxycarbonyloxymethoxy)phosphonomethoxy]-propyl}-purine;
2-amino-6-(4-methoxyphenylthio)-9-{2-[bis(isobutyloxycarbonyloxymethoxy)phosphonomethoxy]-ethyl}-purine;
2-amino-6-(4-methoxyphenylthio)-9-{2-[bis(neopentyloxycarbonyloxymethoxy)phosphonomethoxy]-ethyl}-purine;
2-amino-6-(4-methoxyphenylthio)-9-{2-[bis(pentyl-3-oxycarbonyloxymethoxy)phosphonomethoxy]-ethyl}-purine;
2-amino-6-(4-methoxyphenylthio)-9-{2-[bis(cyclopentyloxycarbonyloxymethoxy)phosphonomethoxy]-propyl}-purine; and
2-amino-6-(4-methoxyphenylthio)-9-{2-[bis(cyclohexyloxycarbonyloxymethoxy)phosphonomethoxy]-propyl}-purine;
or a pharmaceutically acceptable salt, isomer, hydrate or solvate thereof.

According to any embodiment of the first aspect of the present invention, the present invention provides an acyclic nucleoside phosphonate derivative selected from the group consisting of:
2-amino-6-(4-methoxyphenylthio)-9-{2-[bis(propionyloxymethoxy)phosphonomethoxy]-ethyl}-purine ($I_1$);
2-amino-6-(4-methoxyphenylthio)-9-{2-[bis(isobutanoyloxymethoxy)phosphonomethoxy]-ethyl}-purine ($I_2$);
2-amino-6-(4-methoxyphenylthio)-9-{2-[bis(pivaloyloxymethoxy)phosphonomethoxy]-ethyl}-purine ($I_3$);
2-amino-6-(4-methoxyphenylthio)-9-{2-[bis(cyclohexylformyloxymethoxy)phosphonomethoxy]-ethyl}-purine ($I_4$);
(R)-2-amino-6-(4-methoxyphenylthio)-9-{2-[bis(pivaloyloxymethoxy)phosphonomethoxy]-propyl}-purine ($I_5$);
2-amino-6-(4-methoxyphenylthio)-9-{2-[bis(ethyloxycarbonyloxymethoxy)phosphonomethoxy]-ethyl}-purine ($I_6$);
2-amino-6-(4-methoxyphenylthio)-9-{2-[bis(propyloxycarbonyloxymethoxy)phosphonomethoxy]-ethyl}-purine ($I_7$);
2-amino-6-(4-methoxyphenylthio)-9-{2-[bis(isopropyloxycarbonyloxymethoxy)phosphonomethoxy]-ethyl}-purine ($I_8$);
2-amino-6-(4-methoxyphenylthio)-9-{2-[bis(isobutyloxycarbonyloxymethoxy)phosphonomethoxy]-ethyl}-purine ($I_9$);
2-amino-6-(4-methoxyphenylthio)-9-{2-[bis(neopentyloxycarbonyloxymethoxy)phosphonomethoxy]-ethyl}-purine ($I_{10}$);
2-amino-6-(4-methoxyphenylthio)-9-{2-[bis(pentyl-3-oxycarbonyloxymethoxy)phosphonomethoxy]-ethyl}-purine ($I_{11}$);
2-amino-6-(4-methoxyphenylthio)-9-{2-[bis(cyclohexyloxycarbonyloxymethoxy)phosphonomethoxy]-ethyl}-purine ($I_{12}$);
(R)-2-amino-6-(4-methoxyphenylthio)-9-{2-[bis(isopropyloxycarbonyloxymethoxy)phosphonomethoxy]-propyl}-purine ($I_{13}$); and
2-amino-6-(4-methoxyphenylthio)-9-{2-[bis(cyclohexyloxycarbonyloxymethoxy)phosphonomethoxy]-propyl}-purine ($I_{14}$);
or a pharmaceutically acceptable salt, isomer, hydrate or solvate thereof.

According to any embodiment of the first aspect of the present invention, the present invention provides an acyclic nucleoside phosphonate derivative which is selected from the compounds of the examples of the present application, or a pharmaceutically acceptable salt, isomer, hydrate or solvate thereof.

The second aspect of the present invention is to provide a process for preparing an acyclic nucleoside phosphonate derivative or a pharmaceutically acceptable salt, isomer, hydrate or solvate thereof according to any embodiment of the first aspect of the present invention, comprising the following steps:
(i) reacting the compound of formula

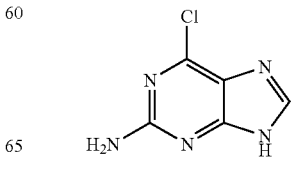

with the compound of formula

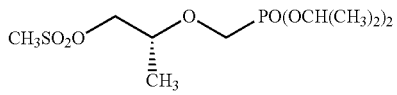

or the compound of formula

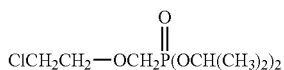

to obtain a compound of the following Formula II:

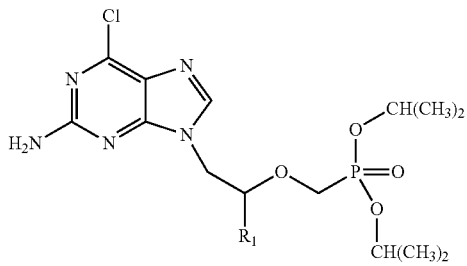

in a suitable solvent (e.g., DMF), in the presence of a suitable reagent (e.g., DBU (i.e., bicyclic amidine), especially when $R_1$ is hydrogen) or potassium carbonate (especially when $R_1$ is methyl), at an elevated temperature (e.g., 60-140° C., for example 80-120° C., or for example 80-100° C.);

ii) reacting the compounds of Formula II with the compound of formula

to obtain a compound of the following Formula III:

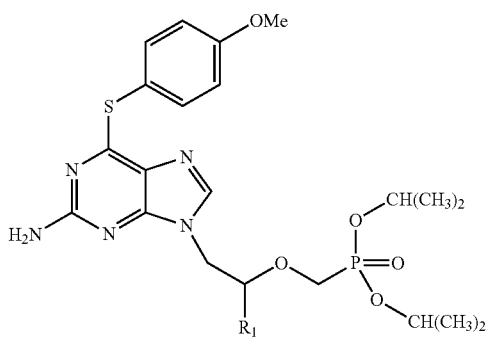

in a suitable solvent (e.g., DMF), in the presence of an organic base (e.g., triethylamine), at an elevated temperature (e.g., 50-120° C., for example 60-100° C.);

iii) reacting the compounds of Formula III with an alkylhalosilane (e.g., trimethylbromosilane) to obtain a free acid compound of the following Formula IV:

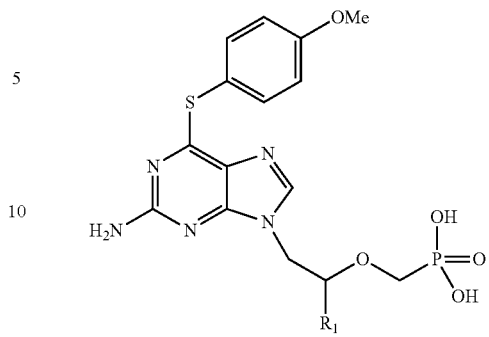

at a temperature of 10-40° C. (e.g., room temperature);

iv) reacting the compounds of Formula IV with an alkanoyloxymethyl halide or an alkyloxycarbonyloxymethyl halide (e.g., chloride, such as

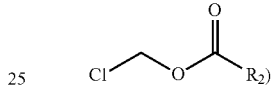

to obtain a compound of the Formula I:

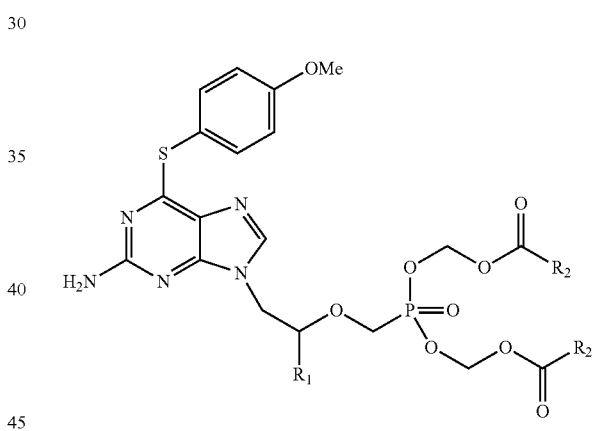

at a temperature of 10-40° C. (e.g., room temperature); and optionally v) subjecting the obtained compound of Formula I to a step of separation, purification, or formulation of a pharmaceutically acceptable salt, hydrate or solvate, wherein $R_1$ and $R_2$ have the meaning as defined in any embodiment of the first aspect of the present invention.

The third aspect of the present invention provides a pharmaceutical composition comprising a therapeutically and/or prophylactically effective amount of an acyclic nucleoside phosphonate derivative or a pharmaceutically acceptable salt, isomer, hydrate or solvate thereof according to any embodiment of the first aspect of the present invention, and optionally one or more pharmaceutically acceptable carriers or excipients. The pharmaceutical compositions of the present invention may be solutions, tablets, capsules or injections; and these pharmaceutical compositions can administered by injection route or oral route. In one embodiment of the third aspect of the present invention, the compounds of Formula I of the present invention or its pharmaceutical composition is preferably administered by oral route.

The fourth aspect of the present invention provides a use of an acyclic nucleoside phosphonate derivative or a pharmaceutically acceptable salt, isomer, hydrate or solvate thereof according to any embodiment of the first aspect of the present invention, or a pharmaceutical composition according to any embodiment of the third aspect of the present invention, in the manufacture of a medicament for the treatment and/or prophylaxis of a disease associated with a viral infection. According to the use of any embodiment of the fourth aspect of the present invention, the virus is hepatitis viruses, such as hepatitis B virus. According to the use of any embodiment of the fourth aspect of the present invention, the disease associated with a viral infection is hepatitis, such as hepatitis B.

The fifth aspect of the present invention provides a method for the treatment and/or prophylaxis of a disease associated with a viral infection in a mammal in need thereof, comprising administering to the mammal in need thereof a therapeutically and/or prophylactically effective amount of an acyclic nucleoside phosphonate derivative or a pharmaceutically acceptable salt, isomer, hydrate or solvate thereof according to any embodiment of the first aspect of the present invention, or a pharmaceutical composition according to any embodiment of the third aspect of the present invention. In one embodiment according to the fifth aspect of the present invention, the disease associated with a viral infection is hepatitis, such as hepatitis B.

DETAILED DESCRIPTION OF THE INVENTION

The various aspects and features of the present invention are further illustrated as follows.

All cited references are incorporated herein by reference, and if any meanings expressed in those references are inconsistent with those in the present invention, the expressions of the present invention should prevail. In addition, the terms and phrases used in the present invention have the common meaning well known by those skilled in the art, unless the terms and phrases are further explained and illustrated in the invention. If the mentioned terms and phrases have a meaning different from those known in the art, the meaning defined in the present invention should prevail.

The terms "halo", "halogen", "Hal" or "halogenated" used herein refer to fluorine, chlorine, bromine and iodine.

The terms "alkyl", "alkenyl" and "alkynyl" used herein have the common meaning well known in the art, that is, they are straight or branched hydrocarbon groups, for example but not limited to methyl, ethyl, propyl, isopropyl, n-butyl, sec-butyl, tert-butyl, allyl, propenyl, propinyl, etc., and the "alkyl", "alkenyl" and "alkynyl" may be collectively called as "hydrocarbonyl" or "aliphatic hydrocarbonyl".

The term "$C_1$-$C_8$ alkyl" used herein refers to a substituted or unsubstituted alkyl group with a desired number of carbon atoms, which examples include but are not limited to methyl, ethyl, propyl, isopropyl, butyl, tert-butyl, pentyl, neopentyl.

The term "$C_3$-$C_8$ cycloalkyl" used herein refers to a substituted or unsubstituted cycloalkyl group with a desired number of carbon atoms, such as cyclopropyl, cyclobutyl, cyclopentyl or cyclohexyl.

According to the detailed teachings of the present invention and the common knowledge in synthesis of an organic compound in the art, those skilled in the art can readily synthesize the compounds of Formula I of the present invention.

In one embodiment, when $R_1$=H, the desired compounds of Formula I may be prepared by an exemplary synthetic route illustrated as follows:

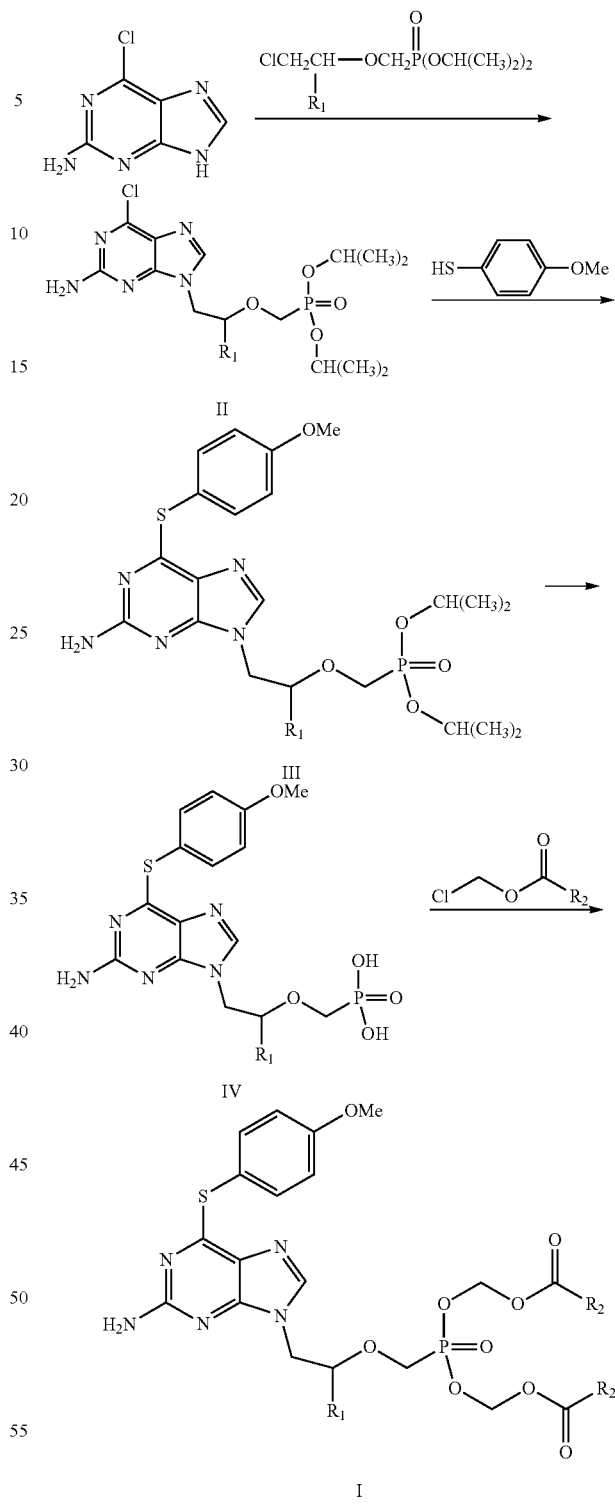

The illustrative synthetic steps comprise dissolving 2-amino-6-chloro-purine and bis-(isopropyl)-phosphoroethyl chloride in DMF, reacting in the presence of DBU at a temperature of 80° C.-100° C. under stirring to obtain an intermediate II; dissolving II and p-methoxyphenylthiol in DMF, and reacting in the presence of triethylamine at a temperature of 60° C.-100° C. under stirring to obtain a p-methoxyphenylthio substituted derivative III; reacting III with trimethylbromosilane at room temperature under stirring to hydrolyze the isopropyl ester so as to obtain a free acid IV, and reacting IV with alkanoyloxymethyl chloride or alkyloxycarbonyloxymethyl chloride at room temperature so as to obtain the desired compound I.

In another embodiment, when $R_1=CH_3$, the desired compounds of Formula I may be prepared by an exemplary synthetic route illustrated as follows:

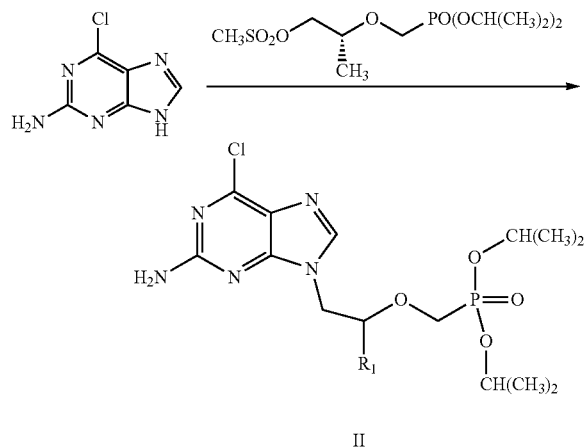

dissolving 2-amino-6-chloro-purine and diisopropyl (R)-{1-methyl-2-[(1-methylsulfonyloxy)ethoxy]methyl}phosphonate ester in DMF, reacting in the presence of potassium carbonate at a temperature of 80° C.-120° C. under stirring to obtain an intermediate II, and then the subsequent procedures may be performed according to the synthetic procedures as described hereinbefore for the compounds of Formula I wherein $R_1=H$.

In the processes for the synthesis of the compounds of Formula I of the present invention, all the raw materials used in the reaction may be prepared and obtained by those skilled in the art according to the knowledge in the art, or may be obtained by the methods well known in the art, or may be obtained commercially. The intermediates, raw materials, reagents and reaction conditions used in the above reaction schemes may be suitably changed by those skilled in the art according to the knowledge in the art. Alternatively, those skilled in the art can also synthesize the other compounds of Formula I which are not specifically listed herein according to the process of the second aspect of the present invention.

The compounds of Formula I of the present invention may be used in a form of itself or a form of its pharmaceutically acceptable salt or solvate. The pharmaceutically acceptable salt of the compounds of Formula I include conventional salts formed with pharmaceutically acceptable inorganic acids or organic acids, or inorganic alkalis or organic alkalis. Suitable examples of acid addition salts include the salts formed with hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methane sulfonic acid, naphthyl-2-sulfonic acid, benzene sulfonic acid, hydroxybenzoic acid, hydroiodic acid, malic acid, tannic acid, etc. The pharmaceutically acceptable salts include its inorganic or organic salts, including but not being limited to: hydroiodate, bisulfate, biphosphate, butyrate, oxalate, trimethylacetate, adipate, alginate, picrate, aspartate, gluconate, esylate, tosylate, pamoate, pyruvate, glycolate, trifluoroacetate, p-aminosalicylate, pamoate, and ascorbate, etc. Suitable examples of alkali addition salts include salts formed with sodium, lithium, potassium, magnesium, aluminum, calcium, zinc, N,N'-dibenzylethylenediamine, chloroprocaine, choline, diethanolamine, ethylenediamine, N-methylglucamine, procaine, etc. When the compounds of the present invention are mentioned, they include the compounds of Formula I and pharmaceutically acceptable salts or solvates thereof. The free base forms of the compounds of the present invention may be slightly different from their salts in some physical properties (e.g., solubility in polar solvent), but for the object of the present invention, their acid salts and their free base forms are equivalent. (see: for example, S. M. Berge, et al., "Pharmaceutical Salts," J. Pharm. Sci., 66: 1-19 (1977), which is incorporated in the text by reference. The compounds of the present invention or pharmaceutically acceptable salts thereof can form solvates, such as hydrates, alcoholates, etc.

According to the present invention, the compounds of Formula I of the present invention may be used in manufacture of a medicament for the treatment of infections caused by hepatitis virus (such as hepatitis B virus).

The term "composition" used herein refers to a product comprising designated components in designated amounts, and any product directly or indirectly formed with designated components in designated amounts. According to the present invention, the "composition" refers to "pharmaceutical composition".

The compounds of Formula I of the present invention further comprise isomers, racemics, enantiomers, diastereomers, enantiomers-enriched product, solvates, and esters thereof, and the compounds of Formula I of the present invention and isomers, racemics, enantiomers, diastereomers, enantiomers-enriched product, solvates and esters thereof can further form solvates, such as hydrates, alcoholic solvates, etc. The compounds can further be prodrugs or in form of capable of releasing the active ingredient after in vivo metabolism. It is common knowledge for a skilled in the art to select and prepare suitable prodrug derivatives. Generally, for the purpose of the present invention, solvates of pharmaceutically acceptable solvents such as water and ethanol are equivalent to those not in forms of solvates.

The actual dose level of various active ingredients in a pharmaceutical composition of the present invention may be varied so that the resultant amount of active compounds can lead to desired therapeutical reactions in specific patients, dosage forms and administration modes. The dose level must be determined according to the activity of specific compound, administration route, severity of disease to be treated, and conditions and past medical history of patients. However, a conventional method in the art is to increase gradually the dose of compound from a level lower than that for achieving desired therapeutical effects to a level enough to achieve the desired therapeutical effects.

When used in the aforementioned or other treatment and/or prophylaxis, a compound of the present invention in a therapeutically and/or prophylactically effective amount may be used in form of pure compound, or in form of pharmaceutically acceptable esters or predrugs thereof (if they exist). Alternatively, the compound may be administered by a pharmaceutical composition comprising the compound and one or more pharmaceutically acceptable excipients. The term a compound of the present invention in a "therapeutically and/or prophylactically effective amount" means that the compound is in an amount sufficient to achieve prophylactically and/or therapeutically reasonable ratio of effect/risk. It should be understood that the total amount per day of the compound or composition of the present invention must be determined by a physician within the range of reliable medical decisions. As for any specific patients, the specific therapeutically amount must be determined based on various factors, including the diseases to be treated and severity thereof, the activity of the used specific compound, the used specific composition, the age, body weight, general health status, gender and food of patient, the administration time and route and excretory rate of the used specific compound, the drug(s) administered in combination or simultaneously with the specific compound, and similar factors well known in the art of medicine. For example, it is a common method in the art to increase gradually the dose of compound from a level lower than that for achieving desired therapeutic effects to a level enough to achieve the desired therapeutic effects. In general, the dose of a compound of Formula I for mammals especially human may be 0.001-1000 mg/kg body weight per day, such as 0.01-100 mg/kg body weight per day, 0.01-10 mg/kg body weight per day.

The compounds or pharmaceutically acceptable salts thereof of the present invention may be administered alone or in form of pharmaceutical composition. The pharmaceutical composition of the present invention may be in various suitable dosage forms formulated according to administration routes. The use of one or more physiologically acceptable carriers, including excipients and additives, is advantageous for processing active compounds to form pharmaceutically acceptable preparations. Suitable preparation forms depend on the selected administration routes, and may be prepared according to the knowledge in the art.

Hence, a pharmaceutical composition comprising an effective amount of the compound of the present invention may be prepared by using a pharmaceutically acceptable carrier well-known by those skilled in the art. The present invention further provides a pharmaceutical composition comprising the compound of the present invention formulated with one or more non-toxic pharmaceutically acceptable carrier. The pharmaceutical composition may be specifically formulated in solid or liquid form for oral administration, parenteral injection or rectal administration.

The routes of administration may be oral, parenteral or topical administration, preferably oral and injection administration. Drug preparations suitable for oral administration comprise capsules and tablets. For a patient with difficulty to swallow, sublingual tablets or other preparations for non-deglutitive administration may be used. The compounds of the present invention may be formulated for parenteral administration or cutaneous penetration administration or transmucosal administration. Those skilled in the art would understand, the compounds of the present invention can use a suitable drug delivery system (DDS) to achieve more advantageous effects.

Specifically, the pharmaceutical composition of the present invention may be administered orally, rectally, parenterally, rectally, parenterally, endoluminally, endovaginally, intraperitoneally, topically (such as via powder, ointment or drops), buccally to a human or other mammal, or administrated as oral spray or nasal spray. The term "parenteral" in the context refers to administration manners including intravenous, intramusculary, intraperitoneal, intrathoracic, subcutaneous and intraarticular injection or transfusion.

The composition suitable for parenteral injection can comprise physiologically acceptable sterile aqueous or nonaqueous solvent, dispersant, suspending agent, or emulsifying agent, as well as sterile dispersant for reforming a sterile injectable solution or dispersion. The examples of suitable aqueous or nonaqueous carriers, diluents, solvents or media include water, ethanol, polyols (propylene glycol, polyethylene glycol, glycerol, etc.), vegetable oil (such olive oil), injectable organic esters such as ethyl oleate and suitable mixtures thereof.

These compositions can further comprise excipients, such as preservative, wetting agent, emulsifying agent and dispersant. The use of various antibacterial agents and antifungal agents, such as nipagins, nautisan, phenol, sorbic acid, etc. can ensure effects of combating microorganisms. It is also desired to comprise isotonizing agents such as sugars, sodium chloride, etc. The use of substances for absorption delay, such as aluminum monostearate and gelatin, can achieve the prolonged absorption of injectable dosage form.

Besides active compound, the suspension can further comprise a suspending agent, such as ethoxylated isooctadecanol, polyoxyethylene sorbitol and polyoxyethylene sorbitan, microcrystalline cellulose, meta-aluminum hydroxide, bentonite, agar and tragacanth gum, or mixtures of these substances.

In some cases, it is desired to reduce the absorption rate of subcutaneously or intramuscularly administered drug for prolonging the effect of drug. This may be reached by using a liquid suspension of crystal or amorphous form with poor water solubility. Thus, the absorption rate of drug depends on its dissolution rate, while the dissolution rate depends on the size and form of crystal. Or, the delayed absorption of drug in parenteral administration may be reached by dissolving or dispersing the drug in an oil medium.

An injectable depot dosage form may be prepared by forming microcapsule substrate of drug in a biodegradable polymer such as polylactide-polyglycolide. The release rate of drug may be controlled according to the ratio of drug to polymer and the properties of the specifically used polymer. Other examples of biodegradable polymer comprise poly (orthoesters) and poly(anhydrides). The injectable depot dosage form can also be prepared by embedding drug in a liposome or microemulsion compatible to body tissues.

The injectable preparation may be sterilized by filtration using a bacterial filter or by incorporating a sterilizing agent in the form of a sterile solid composition, and the solid composition may be dissolved or dispersed in sterile water or other sterile injectable media before clinical application.

The compound of the present invention or composition thereof may be administered orally or parenterally. Those for oral administration may be tablets, capsules, coated dosage form, and pharmaceutical preparations for parenteral administration may be injections and suppository. These preparations are prepared according to methods well-known by those skilled in the art. In order to manufacture tablets, capsules and coated dosage forms, the used excipients are commonly used excipients, such as starch, gelatin, arabic gum, silica, polyethylene glycol, the solvents used for liquid dosage forms are water, ethanol, propylene glycol, vegetable oils (such as corn oil, peanut oil, oliver oil, etc.). The preparations comprising the compound of the present invention can further comprise other excipients, such as surfactants, lubricants, disintegrants, preservatives, correctants and pigments, etc. In tablets, capsules, coated dosage forms, injections and suppositories, the dose of the compounds of Formula I of the present invention is expressed in an amount of the compound existed in unit dosage form. In unit dosage form, the amount of the compounds of Formula of the present invention usually is 1-5000 mg, a preferable unit dosage form contains 10-500 mg, a more preferable unit dosage form contains 20-300 mg. Specifically, the solid dosage form for oral administration as provided in the present invention comprise capsules, tablets, pills, powders and granules. In such solid dosage forms, the active compound may be mixed with at least one inert pharmaceutically acceptable excipient or carrier such as sodium citrate or dicalcium phosphate and/or the following substances: a) filler or bulking agent, such as starch, lactose, sucrose, glucose, mannitol and silicic acid; b) binding agent, such as carboxymethyl cellulose, alginate, gelatin, polyvinyl pyrrolidone, sucrose, and arabic gum; c) humectant, such as glycerol; d) disintegrating agent, such as agar, calcium carbonate, potato or cassava starch, alginic acid, some silicates and sodium carbonate; e) solution blocking agent, such as paraffin wax; f) absorption accelerator, such as quaternary ammonium compounds; g) wetting agent, such as cetanol and glycerol monostearate; h) adsorbent, such as kaolin and bentonite; and i) lubricant, such as talc powder, calcium stearate, magnesium stearate, solid polyethylene glycol, sodium dodecylsulfate and their mixtures. In the cases of capsules, tablets and pills, these dosage forms may also comprise a buffering agent.

A solid composition of similar type uses excipients such as lactose and high molecular weight polyethylene glycol which can also be used as fillers of soft capsules and hard capsules.

The solid dosage forms of tablets, dragees, capsules, pills and granules may be prepared with coating agents and shell materials such as enteric coating materials and other coating materials well-known in the field of medical preparations. These solid dosage forms can optionally comprise sunscreening agent, and theft composition can allow they merely or preferentially release active ingredient at some sites of intestinal tract optionally in a delayed manner. Examples of embedding composition comprise high molecular materials and waxes. If appropriate, the active compound may be formulated in form of microcapsules with one or more aforementioned excipients.

The liquid dosage form for oral administration comprises pharmaceutically acceptable emulsifying agent, solvent, suspending agent, syrup and elixir. Besides the active compound, the liquid dosage form may further comprise an inert diluent commonly used in the art, such as water or other solvent, solubilizer and emulsifying agent, such as ethanol, isopropanol, ethyl carbonate, ethyl acetate, benzyl alcohol, benzyl benzoate, propylene glycol, butane-1,3-diol, dimethyl formamide, oils (such as cottonseed oil, peanut oil, corn oil, embryo oil, olive oil, castor oil, and sesame oil), glycerol, tetrahydrofurfuryl alcohol, fatty acid esters of polyethylene glycol and sorbitan, and their mixtures. Besides inert diluents, the compositions for oral administration can further comprise excipients, such as wetting agents, emulsifying agents and suspending agents, sweeting agents, correctants and flavors.

The composition for rectal or vaginal administration is preferably a suppository. The suppository may be prepared by mixing the compound of the present invention with a suitable non-irritative excipient or carrier, such as cocoa butter, polyethylene glycol or suppository wax, they may be solid at room temperature, but liquid at body temperature, and can release active compound in rectal lumen or vaginal canal.

It is also desired to use the compound of the present invention for topical administration. The dosage form of the compound of the present invention for topical administration comprises powder, spray, ointment and inhalation. The active compound and a pharmaceutically acceptable carrier may be mixed under sterile conditions with any desired preservative, buffering agent or propellant. Ophthalmic preparation, eye salve, powder and solution are all in the scope of the present invention.

The compound of the present invention may be administered in a form of liposome. It is well known in the art, liposome usually is prepared by using phospholipid or other lipids. Liposome is formed with monolayer or multilayer hydrated liquid crystal which is dispersed in an aqueous medium. Any non-toxic, physiologically acceptable and metabolizable lipids capable of forming liposome may be usable. The composition of the present invention in liposome form can comprise stabilizing agent, preservative, excipient, besides the compound of the present invention. Preferable lipids are natural and synthetic phospholipids and phosphatidylcholines (lecithin), they may be used solely or together. The methods for forming liposome are well-known in the art. References may be seen, for example, Prescott, Ed., Methods in Cell Biology, Volume XIV, Academic Press, New York, N.Y. (1976), p. 33.

The present inventors have surprisingly found that the acyclic nucleoside phosphonate derivatives of Formula I have a good activity against viruses such as hepatitis viruses, especially hepatitis B virus, and an unexpected in vivo performances.

ILLUSTRATIVE MODES FOR CARRYING OUT THE INVENTION

The present invention is further illustrated by the following examples, but the scope of the present invention is not limited to these examples. Those skilled in the art would understand that the present invention may be changed or modified without departing from the spirit and scope of the present invention.

The materials and experimental methods used in the experiments are generally and/or specifically described in the present invention. Although most of the materials and procedures for achieving the object of the present invention are well known in the art, they are still described in detail as much as possible.

Example 1

Preparation of 2-(diisopropyl)-phosphonomethoxy)ethyl chloride

The synthetic scheme is as follows:

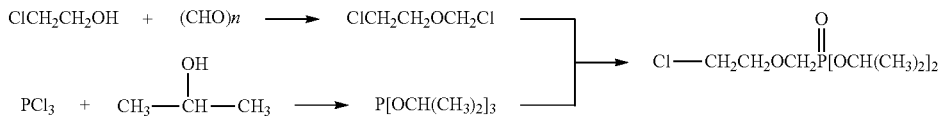

In a 150 ml three-necked bottle, 84.6 g (70.5 ml, 1.05 mol) of 2-chloroethanol and 31.6 g (1.09 mol) of pulverized paraformaldehyde were added, and the mixture was supplied with dry hydrogen chloride gas under stirring for 24 h. After the end of stirring, the reaction liquid was separated into two layers, and the lower layer was taken out and dried over calcium chloride. After filtration, the filtrate was subjected to a fractional distillation at a reduced pressure, and the fraction with a boiling range of 80-84° C./28-30 mmHg was collected to obtain 74.3 g of chloromethyl-2-chloroethyl ether.

In a 300 mL reaction bottle, 18 g (0.3 mol) of isopropanol, 23.7 g (0.3 mol) of pyridine and 100 ml of petroleum ether were added, and the mixture was cooled in ice-bath. Under vigorous agitation, 13.8 g (0.1 mol) of a solution of phosphorus trichloride in 40 ml petroleum ether was added dropwise. After the end of addition, the reaction was performed in a 50° C. oil-bath under stirring for 1 h, then the solid was filtered out, the filtrate was distilled at a reduced pressure to remove the solvent, the residue was distilled at a reduced pressure, and the fraction of 106-108° C./60 mmHg was collected to obtain 15.8 g of triisopropylphosphite.

8.3 g (0.064 mol) of chloromethyl-2-chloroethyl ether was added to a 100 ml three-necked bottle, the mixture was heated and stirred in 90° C. oil-bath, and 15.8 g (0.076 mol) of isopropyl phosphorite was added dropwise. After the end of addition, the reaction was performed in 125° C. oil bath under stirring for 4 h, and the completion of reaction was detected by a silica gel thin layer chromatography (the developing solvent was ethyl acetate, $R_f$=0.6). By distillation at a reduced pressure, the fraction of 118-122° C./1.5 mmHg was collected to obtain 13.5 g of 2-(diisopropyl-phosphonomethoxy)-ethyl chloride.

Example 2

Preparation of diisopropyl (R)-{1-methyl-2-[1-methylsulfonyloxy)ethyloxy]methyl}phosphonate The synthetic scheme is as follows:

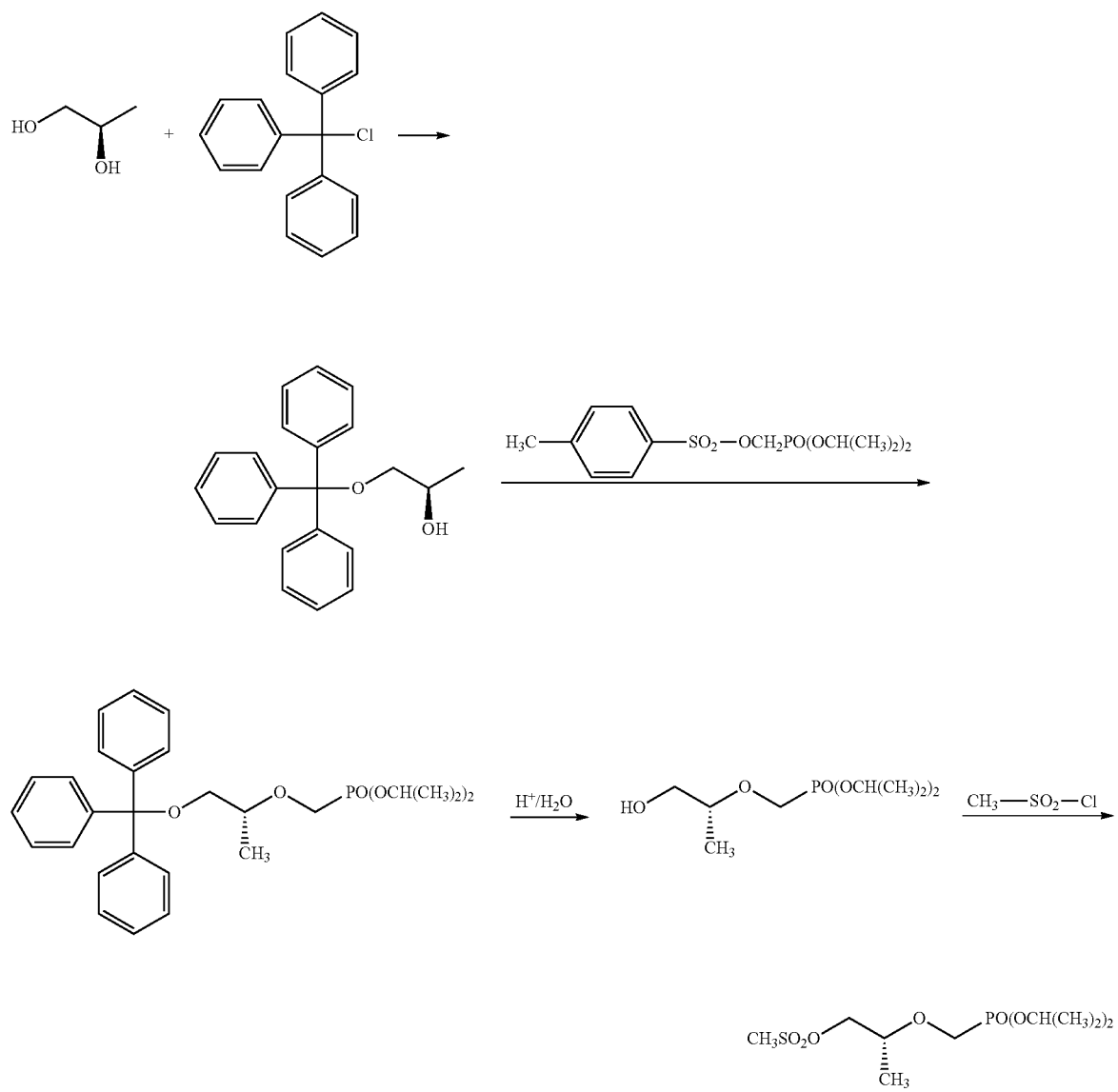

In a 1000 ml bottle, 24.0 g (0.315 moL) of (R)-1,2-propylene glycol, 0.25 g of N,N-dimethylaminopyridine, 350 mL of dichloromethane and 46.0 g (0.45 moL) of triethylamine were added, the mixture was cooled in ice-bath, and stirred with a magnetic agitator. 88.7 g (0.315 moL) of triphenylchloromethane was added in portions within about 1 h, the ice-bath was removed after 1.5 h, and the temperature was elevated to room temperature at which the reaction was performed for about 15 h (until triphenylchloromethane was disappeared by TLC detection). Distilled water (100 mL) was added to dissolve the triethylamine hydrochloride yielded during the reaction, and the mixture was then transferred into a separatory funnel for layering. The oil phase was washed in order with 5% sodium bicarbonate (2×100 ml) and distilled water (100 ml), dried over anhydrous sodium sulfate, filtered, and the filtrate was distilled at a reduced pressure to remove the solvent to obtain 96.6 g of (R)-1-O-triphenylmethyl-1,2-propylene glycol, which was directly used in the next reaction step.

The 96.6 g (about 0.30 mol) of (R)-1-O-triphenylmethyl-1,2-propylene glycol crude product was added to 500 ml of anhydrous tetrahydrofuran, the mixture was stirred with magnetic agitator, and cooled in ice-bath. 11.3 g (70%, 0.33 mol) of sodium hydride was added in portions within about 40 min. 0.5 h later, the ice-bath was removed, the temperature was then elevated to room temperature at which the reaction was performed for about 2 h, and then heated under slight refluxing for about 3 h until no gas was generated. When the temperature was reduced to below 5° C., 106.2 g (0.30 moL) of diisopropyl p-tosyloxymethylphosphonate in anhydrous tetrahydrofuran (200 ml) was added dropwise within about 0.5 h, the ice-bath was removed after 1 h, and the temperature was then elevated to room temperature at which the reaction was performed for about 30 h. After the end of the reaction, the solvent was removed by rotational evaporation, then ethyl acetate (250 ml) and distilled water (200 ml) were added under stirring until all residual solid was dissolved, and the mixture was then transferred into a separatory funnel for layering. The water phase was extracted again with ethyl acetate (2×70 ml), and the organic layers were combined and dried over anhydrous sodium sulfate. After filtration, the solvent of the filtrate was removed by distillation at a reduced pressure, and the residue was separated by a column chromatography (column chromatography conditions: silica gel 200-300 mesh; eluting agent was petroleum ether:ethyl acetate=10:1 to 5:1) to obtain diisopropyl (R)-[(2-triphenylmethoxy-1-methylethyloxy)-methyl]phosphonate as a transparent yellow oil, 90.6 g. $^1$H-NMR (DMSO-d6, 400 MHz) δ: 7.22-7.48 (m, 15H), 4.51-4.67 (m, 2H), 3.62-3.88 (m, 3H), 2.99 (dd, 1H,), 2.92 (dd, 1H), 1.12-1.28 (m, 12H), 1.07 (d, 3H).

The 90.6 g (0.182 mol) of diisopropyl (R)-[(2-triphenylmethoxy-1-methylethyloxy)methyl]phosphonate as a transparent yellow oil and 80% acetic acid solution (380 mL) were stirred to form a homogeneous solution, which was placed in 85° C. oil-bath and heated. The reaction was performed under stirring for 20 min, and then placed in an ice-bath for overnight to allow the side-product triphenylmethanol sufficiently to precipitate. After filtration, the filter cake was washed with 80% acetic acid solution (3×15 ml), and the filtrates were combined, and distilled at a reduced pressure to remove acetic acid and water. The residue was added to ethyl acetate (250 ml), and the mixture was washed with saturated brine (2×50 ml) to obtain an oil layer, which was dried over anhydrous sodium sulfate, and filtered. The filtrate was distilled at a reduced pressure to remove the solvent, and the residue was separated by a column chromatography (column chromatography conditions: silica gel 200-300 mesh; eluting agent was dichloromethane:methanol=50:1 to 10:1), to obtain diisopropyl (R)-[(2-hydroxy-1-methylethyloxy)methyl]phosphonate as a transparent light yellow oil product, 24.1 g.

22.9 g (90 mmol) of diisopropyl (R)-[(2-hydroxy-1-methylethyloxy)methyl]phosphonate was added to 150 mL of dichloromethane, and the mixture was added with 18.4 g (180 mmol) of triethylamine, stirred with a magnetic agitator, and cooled in an ice-bath. 12.6 g (0.108 mol) of methylsulfonyl chloride was added dropwise with a constant pressure funnel within about 1 h, the ice-bath was removed after 0.5 h, the temperature was elevated to room temperature at which the reaction was performed at overnight. Distilled water (70 ml) was added to dissolve the triethylamine hydrochloride generated during the reaction, and the solution was transferred into a separatory funnel for layering. The water phase was extracted with dichloromethane (70 ml), and the oil phases were combined, dried over anhydrous sodium sulfate, and filtered. The filtrate was distilled at a reduced pressure to remove the solvent, and the residue was separated by a column chromatography (column chromatography conditions: silica gel 200-300 mesh; eluting agent was dichloromethane:methanol=60:1 to 20:1) to obtain diisopropyl (R)-{1-methyl-2-[(1-methylsulfonyloxy)ethyloxy]methyl}-phosphonate as a transparent light orange oil, 27.1 g. $^1$H-NMR (CDCl$_3$, 400 MHz) δ: 4.72-4.78 (m, 2H), 4.24 (dd, 1H), 4.18 (dd, 1H), 3.73-3.90 (m, 3H), 3.09 (s, 3H), 1.33-1.37 (m, 12H), 1.24 (d, 3H).

Example 3

Preparation of 2-amino-6-chloro-9-{2-[bis(isopropyloxy)-phosphonomethoxy]-ethyl}-purine (II$_1$)

In 120 ml DMF, 29.3 g of DBU, 32.45 g (0.191 mol) of 2-amino-6-chloropurine were added, stirred at 80° C. for 30 min, then 50 g (0.193 mol) of 2-(diisopropyloxy-phosphonomethoxy)-ethyl chloride was added, the reaction was performed at 100° C. for 8 h, cooled, distilled at a reduced pressure to remove DMF, added with water and ethyl acetate, layered, the water phase was extracted twice with ethyl acetate, the organic phases were combined, dried, separated by silica gel column chromatography, eluted with MeOH:CH$_2$Cl$_2$=1:30, yield 46 g of II$_1$.

Example 4

Preparation of (R)-2-amino-6-chloro-9-{2-[bis(isopropyloxy)-phosphonomethoxy]-propyl}-purine (II$_2$)

In a 500 mL flask (equipped with CaCl$_2$ drying tube), 26.6 g (80.0 mmol) of diisopropyl (R)-{1-methyl-2-[(1-methylsulfonyloxy)ethyloxy]methyl}phosphonate, 200 ml of dimethylformamide and 16.8 g (96.0 mmol) of 2-amino-6-chloropurine and 16.8 g (120 mmol) of anhydrous potassium carbonate were added, stirred with a magnetic agitator, the reaction was performed in 95° C. oil-bath. The oil-bath was removed after 4 h, the filtration was performed after being cooled to room temperature, the filter cake was washed with dimethylformamide (2×30 ml), the filtrates were combined, distilled at a reduced pressure by a rotational evaporator to remove solvent (45° C., 2-5 mmHg), the residue was cooled and added with 250 ml of ethyl acetate and 100 ml of saturated brine, dissolved under stirring, conveyed to a separatory funnel for layering, the oil layer was then washed with saturated brine (2×50 ml), the oil layer was dried over anhydrous sodium sulfate, filtrated, the filtrate was distilled at a reduced pressure with a rotational evaporator to remove solvent, the crude product was separated by a column chromatography (column chromatography condition: silica gel 200-300 mesh; eluting agent was dichloromethane:methanol=100:1 to 50:1 to 15:1), the product obtained by the column chromatography was further recrystallized with ethyl acetate-petroleum ether, filtered, dried to obtain white solid product. The mother liquor was distilled at a reduced pressure to dry by a rotational evaporator, and the second batch of product was obtained by the above-mentioned method for refining crude product. The obtained product in total was 27.1 g, melting point: 130-132° C., specific optical rotation: $[\alpha]_D^{23}$=−44.09 (dichloromethane, c=1.002). $^1$H-NMR (CDCl$_3$, 400 MHz) δ: 7.95 (s, 1H), 5.21 (br s, 2H), 4.64-4.75 (m, 2H), 4.22 (dd, 1H), 4.07 (dd, 1H), 3.85-3.97 (m, 1H), 3.81 (dd, 1H), 3.78 (dd, 1H), 1.12-1.23 (m, 15H).

Example 5

Preparation of 2-amino-6-(4-methoxyphenylthio)-9-(2-phosphonomethoxyethyl)-purine—(IV$_1$)

At room temperature, in 30 ml of DMF, 5 g (12.8 mmol) of II$_1$, 2.6 g (25.6 mmol) of triethylamine and 2.7 g (19.2 mmol) of p-methoxythiophenol were added to sequence, the reaction was performed under the protection of nitrogen gas at 70° C. for 4 h, cooled, distilled at a reduced pressure to remove DMF, added with ethyl acetate and water, stirred, layered, the water layer was extracted with ethyl acetate twice, the organic phases were combined, dried, separated by silica gel column chromatography, eluted with MeOH:CH$_2$Cl$_2$=1:30, to obtain 3.98 g of 2-amino-6-(4-methoxyphenylthio)-9-{2-[bis(isopropyloxy)phosphonomethoxy]-ethyl}-purine (III$_1$) as a viscous liquid.

3.98 g (8 mmol) of III$_1$ was dissolved in 30 ml of acetonitrile, added with 7.25 ml (48 mmol) of trimethylbromosilane at room temperature, the reaction was performed overnight, then added with 5.5 ml of ethanol, stirred for 2 h, to precipitate light yellow solid, filtered, dried under vacuum to obtain 3.3 g of IV$_1$ as yellow solid, melting point: 81.5-82.5° C. $^1$H-NMR (DMSO-d$_6$, 400 MHz) δ: 8.51 (s, 1H), 7.54 (d, 2H), 7.06 (d, 2H), 4.265 (t, 2H), 3.86 (t, 2H), 3.84 (3, 3H), 3.62 (d, 2H).

Example 6

Preparation of (R)-2-amino-6-(4-methoxyphenylthio)-9-{2-[bis(isopropyl)phosphonomethoxy]-propyl}-purine (IV$_2$)

By referring to the method of Example 5, II$_2$ was used to replace II$_1$ and reacted with methoxythiophenol in the presence of triethylamine, separated by silica gel column chromatography to obtain R-2-amino-6-(4-methoxyphenylthio)-9-{2-[bis(isopropyloxy)phosphonomethoxy]-propyl}-purine (III$_2$), yield of 68%.

By referring to the method of Example 5, III$_2$ was deprotected with trimethylbromosilane to obtain IV$_2$, yield 73%. Melting point: 178° C. (dec.). $^1$H-NMR (DMSO-d6, 400 MHz) δ: 8.08 (s, 1H), 7.51 (d, 2H), 7.02 (d, 2H), 4.14 (dd, 1H), 4.05 (dd, 1H), 3.84-3.93 (m, 1H), 3.81 (s, 3H), 3.50-3.64 (m, 2H), 1.05 (d, 3H).

Example 7

Preparation of 2-amino-6-(4-methoxyphenylthio)-9-{2-[bis(propionyloxymethoxy)phosphonomethoxy]-ethyl}-purine (I$_1$)

0.41 g (1 mmol) of IV$_1$, 5.0 ml of anhydrous DMF and 0.2 g (2 mmol) of triethylamine were added to a flask, stirred under nitrogen gas protection at room temperature for 10 min, added with 0.46 g (4 mmol) chloromethyl propionate, the reaction was performed under nitrogen protection at room temperature for 35 h, conveyed to a separatory funnel, added with water (60 ml), extracted with ethyl acetate (3×40 ml), the organic layers were combined, washed with saturated brine (3×40 ml). The oil layer was dried over anhydrous sodium sulfate, filtered to remove drying agent, the filtrate was vacuum concentrated with a rotational evaporator at room temperature, the residue was separated by a column chromatography (column chromatography conditions: silica gel 200-300 mesh; eluting agent was dichloromethane:methanol=80:1 to 40:1), to obtain 0.185 g of I$_1$. $^1$H-NMR (CDCl$_3$, 400 MHz) δ: 7.78 (s, 1H), 7.54 (dd, 2H), 6.96 (dd, 2H), 5.65-5.70 (m, 4H), 4.84 (br s, 2H), 4.28 (t, 2H), 4.09 (t, 2H), 3.86 (s, 3H), 3.92 (m, 2H), 2.37 (q, 4H), 1.12 (t, 6H).

Example 8

Preparation of 2-amino-6-(4-methoxyphenylthio)-9-{2-[bis(isobutanoyloxymethoxy)phosphono-methoxy]-ethyl}-purine (I$_2$)

By referring to the method of Example 7, chloromethyl isobutyrate was used to replace chloromethyl propionate, and reacted with IV$_1$, the reaction product was separated by a column chromatography to obtain I$_2$, yield 31%. $^1$H-NMR (CDCl$_3$, 400 MHz) δ: 7.78 (s, 1H), 7.54 (dd, 2H), 6.96 (dd, 2H), 5.65-5.70 (m, 4H), 4.84 (br s, 2H), 4.28 (t, 2H), 4.09 (t, 2H), 3.86 (s, 3H), 3.92 (m, 2H), 2.53 (m, 2H), 1.13 (d, 12H).

Example 9

Preparation of 2-amino-6-(4-methoxyphenylthio)-9-{2-[bis(pivaloyloxymethoxy)phosphonomethoxy]-ethyl}-purine (I$_3$)

By referring to the method of Example 7, chloromethyl pivalate was used to replace chloromethyl propionate, and reacted with IV$_1$, the reaction product was separated by a column chromatography to obtain I$_3$, yield 35%. $^1$H-NMR (CDCl$_3$, 400 MHz) δ: 7.78 (s, 1H), 7.54 (dd, 2H), 6.96 (dd, 2H), 5.65-5.70 (m, 4H), 4.84 (br s, 2H), 4.28 (t, 2H), 4.09 (t, 2H), 3.86 (s, 3H), 3.92 (m, 2H), 1.23 (s, 9H), 1.22 (s, 9H).

Example 10

Preparation of 2-amino-6-(4-methoxyphenylthio)-9-{2-[bis(cyclohexylformyloxymethoxy)-phosphonomethoxy]-ethyl}-purine (I$_4$)

By referring to the method of Example 7, chloromethyl cyclohexylformate was used to replace chloromethyl propionate, and reacted with IV$_1$, the reaction product was separated by a column chromatography to obtain I$_4$, yield 35%. $^1$H-NMR (CDCl$_3$, 400 MHz) δ: 7.78 (s, 1H), 7.54 (dd, 2H), 6.96 (dd, 2H), 5.65-5.70 (m, 4H), 4.84 (br s, 2H), 4.28 (t, 2H), 4.09 (t, 2H), 3.86 (s, 3H), 3.92 (m, 2H), 2.27 (m, 2H), 1.91 (m, 4H), 1.66 (m, 4H); 1.39-1.47 (m, 12H).

Example 11

Preparation of (R)-2-amino-6-(4-methoxyphenylthio)-9-{2-[bis(pivaloyxymethoxy)phosphonomethoxy]-propyl}-purine (I$_5$)

By referring to the method of Example 7, chloromethyl pivalate reacted with IV$_2$, and the reaction product was separated by a column chromatography to obtain $I_5$, yield 36.5%. $^1$H-NMR (CDCl$_3$, 400 MHZ) $\delta_H$: 7.78 (s, 1H), 7.54 (dd, 2H), 6.96 (dd, 2H), 5.65-5.70 (m, 4H), 4.84 (br s, 2H), 4.18 (dd, 1H), 4.01 (dd, 1H), 3.69-3.96 (m, 6H), 1.23 (s, 9H), 1.22 (s, 9H), 1.19 (d, 3H).

Example 12

Preparation of 6-(4-methoxyphenylthio)-9-{2-[bis(ethyloxycarbonyloxymethoxy)-phosphonomethoxy]-ethyl}-purine ($I_6$)

At room temperature, 1.64 g (4 mmoL) of $IV_1$, 0.8 g (8 mmoL) of triethylamine were added to 12 ml of N-methylpyrrolidone, stirred for 30 min, then 2.2 g (16 mmol) of chloromethyl ethyl carbonate was added, the reaction was performed at 70° C. under stirring for 2 h, cooled, added with 300 ml of 1% citric acid water solution and 500 ml of diethyl ether, stirred, layered, the water layer was extracted with diethyl ether twice, the organic layers were combined, dried, separated by column chromatography, eluted with MeOH:CH$_2$Cl$_2$=1:30, to obtain 0.92 g of $I_6$. $^1$H-NMR (DMSO-d6, 400 MHz) $\delta$: 7.86 (s, 1H), 7.50 (d, 2H), 7.02 (d, 2H), 6.30 (s, 2H, NH$_2$), 5.47-5.78 (m, 4H), 4.24 (m, 4H), 4.28 (t, 2H), 4.09 (t, 2H), 3.95 (m, 2H), 3.83 (s, 3H), 1.30 (m, 6H).

Example 13

Preparation 2-amino-6-(4-methoxyphenylthio)-9-{2-[bis(propyloxycarbonyloxymethoxy)-phosphonomethoxy]-ethyl}-purine ($I_7$)

By referring to the method of Example 12, chloromethyl propyl carbonate was used to replace chloromethy ethyl carbonate, and reacted with $IV_1$, the reaction product was separated by silica gel column chromatography to obtain $I_7$, yield 32%. $^1$H-NMR (DMSO-d6, 400 MHz) $\delta$: 7.86 (s, 1H), 7.50 (d, 2H), 7.02 (d, 2H), 6.30 (br s, 2H), 5.47-5.78 (m, 4H), 4.28 (t, 2H), 4.22 (m, 4H), 4.09 (t, 2H), 3.95 (m, 2H), 3.83 (s, 3H), 1.62 (m, 4H), 0.98 (m, 6H).

Example 14

Preparation of 2-amino-6-(4-methoxyphenylthio)-9-{2-[bis(isopropyloxycarbonyloxy methoxy)-phosphonomethoxy]-ethyl}-purine ($I_8$)

By referring to the method of Example 12, chloromethyl isopropyl carbonate was used to replace chloromethy ethyl carbonate, and reacted with $IV_1$, the reaction product was separated by silica gel column chromatography to obtain $I_8$, yield 27%. $^1$H-NMR (DMSO-d6, 400 MHz) $\delta$: 7.86 (s, 1H), 7.50 (d, 2H), 7.02 (d, 2H), 6.30 (s, 2H, NH$_2$), 5.47-5.78 (m, 4H), 4.83 (m, 2H) 4.28 (t, 2H), 4.09 (t, 2H), 3.95 (m, 2H), 3.83 (s, 3H), 1.26 (s, 6H), 1.24 (s, 6H).

Example 15

Preparation of 2-amino-6-(4-methoxyphenylthio)-9-{2-[bis(isobutyloxycarbonyloxymethoxy)-phosphonomethoxy]ethyl}-purine ($I_9$)

By referring to the method of Example 12, chloromethyl isobutyl carbonate was used to replace chloromethy ethyl carbonate, and reacted with $IV_1$, the reaction product was separated by silica gel column chromatography to obtain $I_9$, yield 20%. $^1$H-NMR (DMSO-d6, 400 MHz) $\delta$: 7.86 (s, 1H), 7.50 (d, 2H), 7.02 (d, 2H), 6.30 (br s, 2H), 5.47-5.78 (m, 4H), 4.28 (t, 2H), 4.11 (d, 4H), 4.09 (t, 2H), 3.95 (m, 2H), 3.83 (s, 3H), 1.87 (m, 2H), 0.97 (m, 12H).

Example 16

Preparation of 2-amino-6-(4-methoxyphenylthio)-9-{2-[bis(neopentyloxycarbonyloxymethoxy)-phosphonomethoxy]-ethyl}-purine ($I_{10}$)

By referring to the method of Example 12, chloromethyl isopropyl carbonate was used to replace chloromethy ethyl carbonate, and reacted with $IV_1$, the reaction product was separated by silica gel column chromatography to obtain $I_{10}$, yield 18%. $^1$H-NMR (DMSO-d6, 400 MHz) $\delta$: 7.86 (s, 1H), 7.50 (d, 2H), 7.02 (d, 2H), 6.30 (br s, 2H), 5.47-5.78 (m, 4H), 4.28 (t, 2H), 4.13 (s, 4H), 4.09 (t, 2H), 3.95 (m, 2H), 3.83 (s, 3H), 0.94 (s, 18H).

Example 17

Preparation of 2-amino-6-(4-methoxyphenylthio)-9-{2-[bis(pentyl-3-oxycarbonyloxymethoxy)-phosphonomethoxy]-ethyl}-purine ($I_{11}$)

By referring to the method of Example 12, chloromethyl (3-pentyl) carbonate was used to replace chloromethy ethyl carbonate, and reacted with $IV_1$, the reaction product was separated by silica gel column chromatography to obtain $I_{11}$, yield 15%. $^1$H-NMR (DMSO-d6, 400 MHz) $\delta$: 7.86 (s, 1H), 7.50 (d, 2H), 7.02 (d, 2H), 6.30 (br s, 2H), 5.47-5.78 (m, 4H), 4.28 (t, 2H), 4.11 (m, 2H), 4.09 (t, 2H), 3.95 (m, 2H), 3.83 (s, 3H), 1.52-1.62 (m, 8H), 0.92 (t, 12H).

Example 18

Preparation of 2-amino-6-(4-methoxyphenylthio)-9-{2-[bis(cyclohexyloxycarbonyloxymethoxy)-phosphonomethoxy]-ethyl}-purine ($I_{12}$)

By referring to the method of Example 12, chloromethyl cyclohexyl carbonate was used to replace chloromethy ethyl carbonate, and reacted with $IV_1$, the reaction product was separated by silica gel column chromatography to obtain $I_{12}$, yield 24%. $^1$H-NMR (DMSO-d$_6$, 400 MHz) $\delta$: 7.86 (s, 1H), 7.50 (d, 2H), 7.02 (d, 2H), 6.30 (br s, 2H), 5.47-5.78 (m, 4H), 4.52-4.61 (m, 2H), 4.28 (t, 2H), 4.09 (t, 2H), 3.95 (m, 2H), 3.83 (s, 3H), 2.55 (m, 2H), 1.80 (m, 4H), 1.15-1.50 (m, 12H).

Example 19

Preparation of (R)-2-amino-6-(4-methoxyphenylthio)-9-{2-[bis(isopropyloxycarbonyloxymethoxy)-phosphonomethoxy]-propyl}-purine ($I_{13}$)

By referring to the method of Example 12, chloromethyl isopropyl carbonate was used to react with $IV_2$, the reaction product was separated by silica gel column chromatography to obtain $I_{13}$, yield 16%. $^1$H-NMR (DMSO-d6, 400 MHz) $\delta$: 7.86 (s, 1H), 7.50 (d, 2H), 7.02 (d, 2H), 6.30 (br s, 2H), 5.47-5.78 (m, 4H), 4.83 (m, 2H), 4.18 (dd, 1H), 4.01 (dd, 1H), 3.85-4.06 (m, 3H), 3.81 (s, 3H), 1.26 (s, 6H), 1.24 (s, 6H), 1.07 (d, 3H).

Example 20

Preparation of 2-amino-6-(4-methoxyphenylthio)-9-{2-[bis-(cyclohexyloxycarbonyloxymethoxy)-phosphonomethoxy]-propyl}-purine ($I_{14}$)

By referring to the method of Example 12, chloromethyl cyclohexyl carbonate was used to react with $IV_2$, the reaction product was separated by silica gel column chromatography to obtain $I_{14}$, yield 21%. $^1$H-NMR (DMSO-$d_6$, 400 MHz) δ: 7.83 (s, 1H), 7.50 (dd, 2H), 7.02 (dd, 2H), 6 (br s, 2H), 5.47-5.78 (m, 4H), 4.52-4.61 (m, 2H), 3.82-4.15 (m, 5H), 3.80 (s, 3H), 1.80 (m, 4H), 1.63 (m, 4H), 1.15-1.50 (m, 12H), 1.05 (d, 3H).

In view of the present invention, especially the teaching of the methods of the above examples and knowledge in the art and references, those skilled in the art can further synthesize the compounds of Formula I that are not exemplified, in particular, can synthesize the specific compounds as aforementioned in the text and the specific compounds as listed in the claims.

Experimental Example 1

Test of In Vitro Activity Against HBV

By an in vitro test method of using Hep G 2.2.15 cells, the inhibition effects and cytotoxicity of the desired compounds to HBV DNA were measured.

Test Method

By using quantitative and real-time fluorescent PCR method, the inhibition effects of the desired compounds to HBV DNA were measured: Hep G 2.2.15 cells were cultured in a DMEM culture medium containing 10% bovine calf serum, incubated in a 5% $CO_2$ incubator, then the cells were inoculated in 96-well plate, cell count $3 \times 10^4$, continuously cultured, when the cell density reached about 80%, the used culture medium was discarded, and new culture media with different drug concentrations were added, in which 3 parallel wells were set; the culture media were exchanged every three days. On the $10^{th}$ day of using drug, 100 μl of supernatant was taken and measured to determine HBV DNA content by quantitative PCR method, calculate 50% inhibition concentration, i.e., $IC_{50}$ value.

The cytotoxicity of the desired compounds were measured by MTT method: Hep $G_2$ cells were cultured in a DMEM culture medium containing 10% bovine calf serum, incubated in a 5% $CO_2$ incubator, then the cells were inoculated in 96-well plate, cell count $5 \times 10^4$, continuously cultured for 3 days, added with new culture media with different drug concentrations, in which 3 parallel wells were set; on the $3^{rd}$ day of adding drugs, MTT was added to 7.5 mg/ml, the culture was kept for further 2 h, the supernatant was discarded, isopropanol containing 10% Tween X-100 was added, 120 μl/well, then added 0.4 μl/well again, enzyme-linked meter was used to measure the absorption at 540 nm, calculate 50% inhibition concentration, i.e., $CC_{50}$ value. The results are shown in Table 1:

TABLE 1

$IC_{50}$ values and $CC_{50}$ values of some exemplary compounds of the present invention

| Compound | $IC_{50}$ (μM) | $CC_{50}$ (μM) |
|---|---|---|
| MCC-478 | 0.016 | >1000 |
| $I_2$ | 0.020 | >1000 |
| $I_3$ | 0.015 | >1000 |
| $I_4$ | 0.012 | >1000 |
| $I_5$ | 0.006 | >1000 |
| $I_8$ | 0.005 | >1000 |
| $I_9$ | 0.021 | >1000 |
| $I_{12}$ | 0.011 | >1000 |
| $I_{13}$ | 0.054 | >1000 |

The compounds of other Examples of the present invention and the specific compounds aforementioned in the present invention and the specific compounds as listed in the attached claims can also achieve results substantively identical to the IC50 values and CC50 values of the compounds of the Examples of the present invention as shown in Table 1.

Experimental Example 2

Comparison of Bioavailability for Oral Administration

SD male rats, body weight 180 to 220 g, 3 rats per group, all animals were fasted for 12 h before administration of drug, the sample to be tested was formulated into a 10 mg/ml suspension solution of 1% sodium carboxymethylcellulose, intragastrically administered in a dose equivalent to 20 mg/kg for 2-amino-6-(4-methoxyphenylthio)-9-(2-phosphonomethoxyethyl)-purine ($IV_1$, 602076); 602076 was formulated to form 10 mg/ml physiological saline solution, administered by injection via caudal vein in a dose of 10 mg/kg. Blood samples in an amount of 0.5 ml were collected from eyeground venous plexus of rats before administration and after administration for 0.25, 0.5, 0.75, 1.0, 1.5, 2.0, 3.0, 6.0, 12.0, 24.0 h, and the method of reference document (Clark Chan, et al. Clinical Pharmaco-kinetics of Alamifovir and Its Metabolites Antivicrob Agents Chemother, 2005, 49(5): 1813-1822.) was used to determine the concentrations of 602076 in blood samples collected at different time points.

The blood drug concentration-time data were input to a computer, the parameters of pharmakinetics were calculated by using non-ventricle model method, $AUC_{0-\infty}$ value was calculated by trapezoidal method, and the absolute bioavailability (F) of active metabolite 602076 of various prodrug compounds after oral administration in rats was calculated by using the area under curve ($AUC_{0-\infty}$) of average blood drug concentration-time curve of 602076 as determined with the tested rats separately subjected to oral administration of the tested samples and to intravenous injection of 602076.

$F = AUC_{0-\infty}$(oral administration)/$AUC_{0-\infty}$(intravenous injection)$\times 100\% \times 2$

TABLE 2

Comparison of some exemplary compounds of the present invention in bioavailability of oral administration in rats, expressed in 602076

| Compound | Bioavailability (%, expressed in 602076) |
|---|---|
| MCC-478 | 5.6 |
| $I_2$ | 43.0 |
| $I_3$ | 42.6 |
| $I_4$ | 38.4 |
| $I_8$ | 37.2 |
| $I_9$ | 34.2 |
| $I_{12}$ | 26.8 |

The compounds of other Examples of the present invention and the specific compounds aforementioned in the present invention and the specific compounds as listed in the attached claims can also achieve results substantively identical to the bioavailability values of the compounds of the Examples of the present invention as shown in Table 2.

What is claimed is:

1. An acyclic nucleoside phosphonate derivative of Formula I:

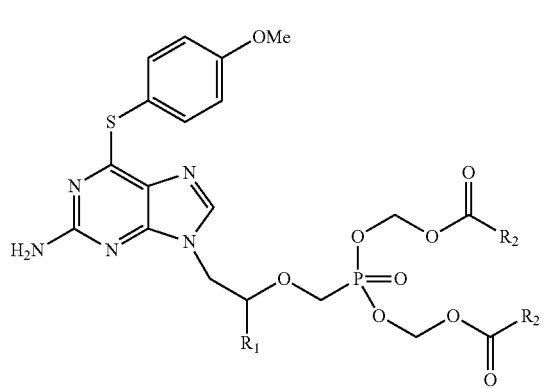

I wherein,
$R_1$ is selected from H or methyl;
each $R_2$ is independently —$OR_3$;
each $R_3$ is independently selected from $C_1$-$C_8$ alkyl, or $C_3$-$C_8$ cycloalkyl;
or a pharmaceutically acceptable salt, enantiomer, diastereomer, hydrate or solvate thereof.

2. The acyclic nucleoside phosphonate derivative of Formula I or a pharmaceutically acceptable salt, enantiomer, diastereomer, hydrate or solvate thereof according to claim 1, wherein the two $R_2$ are the same; or wherein the two $R_2$ are different.

3. The acyclic nucleoside phosphonate derivative of Formula I or a pharmaceutically acceptable salt, enantiomer, diastereomer, hydrate or solvate thereof according to claim 1, wherein $R_3$ for each occurrence is independently selected from $C_1$-$C_6$ alkyl or $C_3$-$C_6$ cycloalkyl.

4. The acyclic nucleoside phosphonate derivative of Formula I or a pharmaceutically acceptable salt, enantiomer, diastereomer, hydrate or solvate thereof according to claim 3, wherein $R_3$ for each occurrence is independently selected from $C_2$-$C_6$ alkyl or $C_4$-$C_6$ cycloalkyl.

5. The acyclic nucleoside phosphonate derivative of Formula I or a pharmaceutically acceptable salt, enantiomer, diastereomer, hydrate or solvate thereof according to claim 1, wherein $R_3$ for each occurrence is independently selected from methyl, ethyl, propyl, isopropyl, butyl, isobutyl tert-butyl, t-butyl n-pentyl, isopentyl, neopentyl, cyclopropyl cyclobutyl, cyclopentyl cyclohexyl, or —$CH(CH_2CH_3)_2$.

6. The acyclic nucleoside phosphonate derivative of Formula I or a pharmaceutically acceptable salt, enantiomer, diastereomer, hydrate or solvate thereof according to claim 5, wherein $R_3$ for each, occurrence is independently selected from ethyl, propyl, isopropyl, butyl, isobutyl, isopentyl, neopentyl, cyclopentyl, cyclohexyl, or —$CH(CH_2CH_3)_2$.

7. The acyclic nucleoside phosphonate derivative of Formula I according to claim 1 which is selected from the group consisting of:

2-amino-6-(4-methoxyphenylthio)-9-{2-[bis(ethyloxycarbonyloxymethoxy)phosphonomethoxy]-ethyl}-purine;

2-amino-6-(4-methoxyphenylthio)-9-{2-[bis(propyloxycarbonyloxymethoxy)phosphonomethoxy]-ethyl}-purine;

2-amino-6-(4-methoxyphenylthio)-9-{2-[bis(isopropyloxycarbonyloxymethoxy)phosphonomethoxy]-ethyl}-purine;

2-amino-6-(4-methoxyphenylthio)-9-{2-[bis(cyclopentyloxycarbonyloxymethoxy)phosphonomethoxy]-ethyl}-purine;

2-amino-6-(4-methoxyphenylthio)-9-{2-[bis(cyclohexyloxycarbonyloxymethoxy)phosphonomethoxy]-ethyl}-purine;

2-amino-6-(4-methoxyphenylthio)-9-{2-[bis(propyloxycarbonyloxymethoxy)phosphonomethoxy]-propyl}-purine;

2-amino-6-(4-methoxyphenylthio)-9-{2-[bis(propyloxycarbonyloxymethoxy)phosphonomethoxy]-propyl}-purine;

2-amino-6-(4-methoxyphenylthio)-9-{2-[bis(isopropyloxycarbonyloxymethoxy)phosphonomethoxy]-propyl}-purine;

2-amino-6-(4-methoxyphenylthio)-9-{2-[bis(isobutyloxycarbonyloxymethoxy)phosphonomethoxy]-ethyl}-purine;

2-amino-6-(4-methoxyphenylthio)-9-{2-[bis(neopentyloxycarbonyloxymethoxy)phosphonomethoxy]-ethyl}-purine;

2-amino-6-(4-methoxyphenylthio)-9-{2-[bis(pentyl-3-oxycarbonyloxymethoxy)phosphonomethoxy]-ethyl}-purine;

2-amino-6-(4-methoxyphenylthio)-9-{2-[bis(cyclopentyloxycarbonyloxymethoxy)phosphonomethoxy]-propyl}-purine; and 2-amino-6-(4-methoxyphenylthio)-9-{2-[bis(cyclohexyloxycarbonyloxymethoxy)phosphonomethoxy]-propyl}-purine;

or a pharmaceutically acceptable salt, enantiomer, diastereomer, hydrate or solvate thereof.

8. The acyclic nucleoside phosphonate derivative of Formula I according to claim 1, which is selected from the group consisting of:

2-amino-6-(4-methoxyphenylthio)-9-{2-[bis(ethyloxycarbonyloxymethoxy)phosphonomethoxy]-ethyl}-purine ($I_6$);

2-amino-6-(4-methoxyphenylthio)-9-{2-[bis(propyloxycarbonyloxymethoxy)phosphonomethoxy]-ethyl}-purine ($I_7$);

2-amino-6-(4-methoxyphenylthio)-9-{2-[bis(isopropyloxycarbonyloxymethoxy)phosphonomethoxy]-ethyl}-purine ($I_8$);

2-amino-6-(4-methoxyphenylthio)-9-{2-[bis(isobutyloxycarbonyloxymethoxy)phosphonomethoxy]-ethyl}-purine ($I_9$);

2-amino-6-(4-methoxyphenylthio)-9-{2-[bis(neopentyloxycarbonyloxymethoxy)phosphonomethoxy]-ethyl}-purine ($I_{10}$);

2-amino-6-(4-methoxyphenylthio)-9-{2-[bis(pentyl-3-oxycarbonyloxymethoxy)phosphonomethoxy]-ethyl}-purine ($I_{11}$);

2-amino-6-(4-methoxyphenylthio)-9-{2-[bis(cyclohexyloxycarbonyloxymethoxy)phosphonomethoxy]-ethyl}-purine ($I_{12}$);

(R)-2-amino-6-(4-methoxyphenylthio)-9-{2-[bis(isopropyloxycarbonyloxymethoxy)phosphonomethoxy]-propyl}-purine ($I_{13}$); and 2-amino-6-(4-methoxyphenylthio)-9-{2-[bis(cyclohexyloxycarbonyloxymethoxy)phosphonomethoxy]-propyl}-purine ($I_{14}$);

or a pharmaceutically acceptable salt, enantiomer, diastereomer, hydrate or solvate thereof.

9. A pharmaceutical composition comprising a therapeutically effective amount of an acyclic nucleoside phosphonate derivative of Formula I or a pharmaceutically acceptable salt, enantiomer, diastereomer, hydrate or solvate thereof according to claim 1, and optionally one or more pharmaceutically acceptable carriers or excipients.

10. A compound for the treatment of a viral infection, which compound is an acyclic nucleoside phosphonate derivative of Formula I or a pharmaceutically acceptable salt, enantiomer, diastereomer, hydrate or solvate thereof according to claim 1, wherein the viral infection is hepatitis B.

11. A method for the treatment of a viral infection in a mammal in need thereof, which method comprises administering to the mammal in need thereof a therapeutically effective amount of an acyclic nucleoside phosphonate derivative or a pharmaceutically acceptable salt, enantiomer, diastereomer, hydrate or solvate thereof according to claim 1, or a pharmaceutical composition according to claim 9, wherein the viral infection is hepatitis B.

12. A process for preparing an acyclic nucleoside phosphonate derivative or a pharmaceutically acceptable salt, enantiomer, diastereomer, hydrate or solvate thereof according to claim 1, which comprises the following steps:

(i) reacting the compound of formula

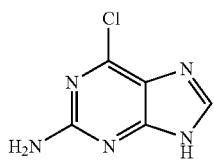

with the compound of formula

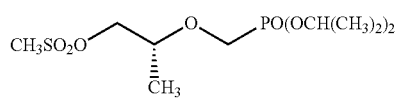

or the compound of formula

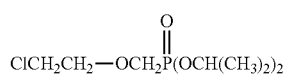

to obtain a compound of Formula II:

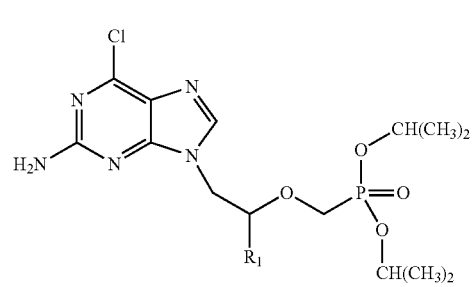

in the presence of a suitable solvent and a base, at a temperature of 60-140° C.;

ii) reacting the compound of Formula II with the compound of formula

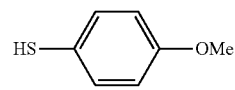

to obtain a compound of Formula III:

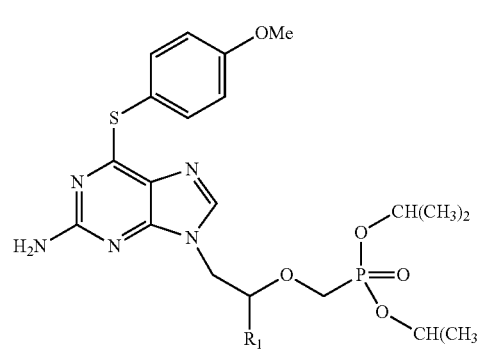

in the presence of a suitable solvent and an organic base, at a temperature of 60-100° C.;

iii) reacting the compound of Formula III with an alkylhalosilane to obtain a free acid compound of the following Formula IV:

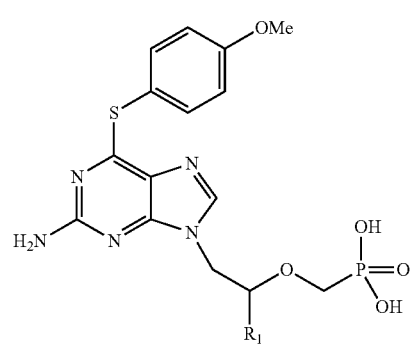

at a temperature of 10-40° C.;

iv) reacting the compound of Formula IV with an alkanoyloxymethyl halide or an alkyloxycarbonyloxymethyl halide to obtain a compound of Formula I:

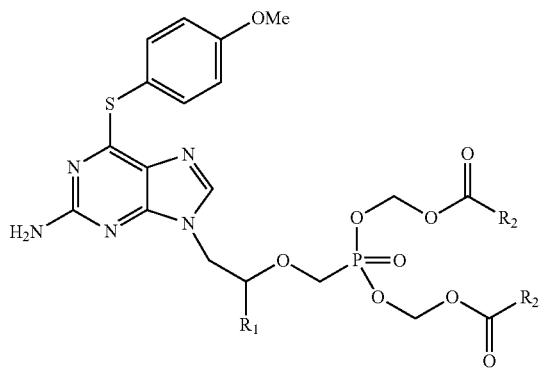

I at a temperature of 10-40° C.; and optionally v) subjecting the obtained compound of Formula I to a step of separation, purification, or formulation into a pharmaceutically acceptable salt, hydrate or solvate, wherein $R_1$ and $R_2$ have the definitions as recited in claim 1.

13. The process of claim 12, wherein the solvent in step (i) is DMF and the base is DBU or potassium carbonate.

14. The process of claim 12, wherein the solvent in step (ii) is DMF and the base is triethylamine.

15. The process of claim 12, wherein the alkylhalosilane in step (iii) is trimethylbromosilane.

16. The process of claim 12, wherein the alkyloxycarbonyloxymethyl halide in step (iv) is

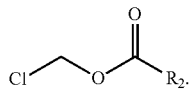

* * * * *